United States Patent [19]

Haberlein et al.

[11] 4,118,352

[45] Oct. 3, 1978

[54] ORGANIC PHOSPHITES, PROCESS FOR THEIR MANUFACTURE AND THEIR USE AS STABILIZERS

[75] Inventors: Harald Häberlein; Herbert Nies; Franz Scheidl, all of Gersthofen, Fed. Rep. of Germany

[73] Assignee: Hoechst Aktiengesellschaft, Frankfurt am Main, Fed. Rep. of Germany

[21] Appl. No.: 796,199

[22] Filed: May 12, 1977

[30] Foreign Application Priority Data

May 13, 1976 [DE] Fed. Rep. of Germany ....... 2621323

[51] Int. Cl.$^2$ ............................ C07F 9/15; C08K 5/52
[52] U.S. Cl. ............................ 260/23 XA; 252/400 A; 252/400 R; 252/406; 252/407; 260/45.8 A; 260/45.8 R; 260/45.85 S; 260/45.95 L; 260/927 R; 260/936; 260/968
[58] Field of Search .............. 260/45.8 R, 927 R, 936, 260/937, 968

[56] References Cited

U.S. PATENT DOCUMENTS

| 3,293,327 | 12/1966 | Hechenbleikner et al. ......... 260/936 |
| 3,737,485 | 6/1973 | Hechenbleikner ............... 260/927 R |
| 3,959,413 | 5/1976 | Schwarzenbach et al. ...... 260/927 R |
| 4,053,541 | 10/1977 | Fischer et al. .................. 260/45.8 R |

OTHER PUBLICATIONS

Shechter et al., Industrial and Engineering Chemistry, Jan. 1956, pp. 86–93.

*Primary Examiner*—Donald E. Czaja
*Assistant Examiner*—R. A. White
*Attorney, Agent, or Firm*—Connolly and Hutz

[57] ABSTRACT

The present invention is related to novel phosphites, their use as stabilizers for organic polymers, furthermore to stabilizer compositions containing these novel phosphites as well as the organic polymers being stabilized therewith. The novel phosphites have a good stabilization effect, especially in combination with known stabilizers, and they are substantially stable against hydrolytical influence. Their volatility and tendency to exudation are very weak.

5 Claims, No Drawings

ORGANIC PHOSPHITES, PROCESS FOR THEIR MANUFACTURE AND THEIR USE AS STABILIZERS

It is generally known that heat and light have a detrimental influence on synthetic high polymers. In the industrial practice, this is prevented by addition of stabilizers and stabilizing additives, whereby synergistic effects are often achieved.

Commonly applied stabilizing additives are, for example, epoxy compounds, antioxidants, polyols, compounds absorbing ultra-violet radiation, and organic phosphites.

However, the known stabilizing additives are very often not entirely satisfactory in the practice, some having a number of shortcomings. For example, a series of known organic phosphites which are used for stabilization purposes show insufficient resistance to hydrolytic influence and a relatively high degree of volatility. Moreover, most of the known phosphites do not meet the requirements of non-toxic properties which become more and more important recently.

It was therefore the object of this invention to find out stabilizers on the basis of organic phosphites the characteristic criteria of which are low volatility, high resistance to hydrolysis, a minimum toxicity, and a high degree of stabilizing activity.

In accordance with this invention there has now been found that, surprisingly, phosphites hitherto unkown, that is, β-hydroxyalkyl ethers of pentaerythrite phosphite, possess the intended advantageous properties to a large extent.

The present invention provides therefore phosphites of the formula

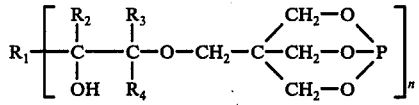

wherein $n$ is 1 or 2, and in the case where $n$ is 1, $R_1$ through $R_4$ are identical or different radicals which may represent (a) from 0 to 3 hydrogen atoms,
(b) phenyl or naphthyl radicals or cycloalkyl radicals having from 5 to 12 carbon atoms, these radicals optionally being substituted by alkyl groups having from 1 to 9 carbon atoms or by 1 to 4 chlorine atoms, and
(c) linear or branched alkyl radicals having from 1 to 60 carbon atoms, optionally being substituted by a phenyl or alkylphenyl group having from 7 to 10 carbon atoms or a cycloalkyl group having from 5 to 12 carbon atoms, the radicals indicated sub (b) and (c) optionally containing ether, thioether, carboxylic acid ester or epoxide groups, halogen substituents or C═C bonds in addition; and/or $R_2$ and $R_3$ optionally being common members of a saturated or unsaturated alkylene chain optionally alkyl- or arylsubstituted and having from 3 to 10 carbon atoms, and the sum of all carbon atoms contained in $R_1$ through $R_4$ being at least 4, but no more than 60; while in the case where $n$ is 2, $R_2$, $R_3$ and $R_4$ are identical or different radicals being as defined above, and $R_1$ is a bivalent organic radical which represents (a) an alkylene chain having from 1 to 10 carbon atoms optionally being substituted by methyl or ethyl groups, and optionally being interrupted by ether, thioether or carboxylic acid ester groups, or
(b) a group of the general formula

—CH$_2$—O—A—O—CH$_2$ wherein A is a phenylene or naphthylene radical optionally substituted by alkyl groups or halogen atoms; an alkylene chain having from 2 to 12 carbon atoms, optionally being substituted by methyl or ethyl groups and optionally being interrupted by ether, thioether or carboxylic acid ester groups; a 1,3- or 1,4-dimethylene-cyclohexane radical; an α,ω-diacylalkylene radical having from 3 to 12 carbon atoms and optionally being substituted by methyl or ethyl groups and optionally being interrupted by ether, thioether or carboxylic acid ester groups or C═C bonds; or a diacylphenylene or diacylnapthylene radical optionally substituted by alkyl groups or halogen atoms; or (c) a group of the formula

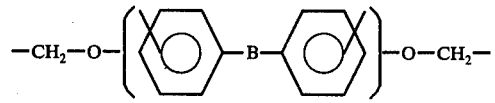

wherein B is —O—, —S—, —CO—, —SO$_2$— or

wherein D and E, being identical or different, are hydrogen atoms or alkyl radicals having from 1 to 6 carbon atoms, or common members of an alkylene chain having from 4 to 6 carbon atoms; or (d) a group of the formula

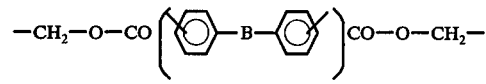

wherein B is as defined sub (c);
and the sum of all carbon atoms contained in the radicals $R_1$ through $R_4$ is at least 4, but does not exceed 60.

The present invention provides furthermore a process for the manufacture of these phosphites, and their use as stabilizers for synthetic high polymers.

A special advantage of the phosphites of the invention resides in their considerably higher resistance to hydrolytic influence as compared to that of many known phosphite stabilizers, a property which imparts to them very good storage stability and improves the weathering properties of the polymer molding compositions so stabilized.

A further advantage is that such phosphites of the present invention that are solid at room temperature impart a better dimension stability under heat to plastic articles processed by means of these phosphites than is obtained using known liquid phosphites.

Also, the use of the phosphites of the present invention reduces substantially tarnishing of the processing machines and the formation of grooves on the shaped articles being produced.

Additional useful properties of the phosphites of the present invention are the general lack of smell, the practical absence of volatility and the lack of tendency to exudation.

The phosphites of the invention are prepared by addition of pentaerythrite phosphite on epoxides. The reaction proceeding according to the following scheme:

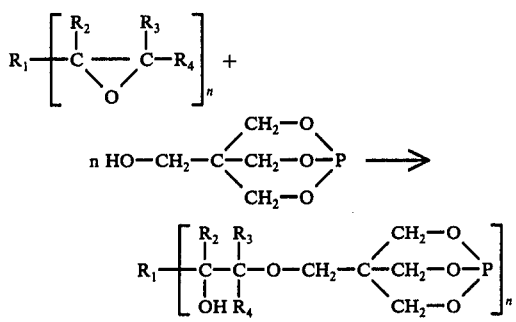

is carried out at temperatures of from 100° to 200° C., preferably from 120° to 160° C., in the presence of acidic or even basic catalysts, for example tin tetrachloride, sulfuric acid or triethylamine; the reaction time is from 2 to 40 hours and is controlled by means of the decreasing epoxide content of the reaction mixture. The amount of catalyst is from 0.002 to 2.0, preferably 0.005 to 0.5 mol %, relative to the pentaerythrite phosphite. The reaction may be carried out in the presence of inert solvents; preferably, it is carried out without solvent in the melt.

The pentaerythrite used as reactant is obtained according to known methods by transesterification of tri-lower alkyl phosphites or of triphenyl phosphite with pentaerythrite.

For the reaction with the corresponding epoxide, there may be used either directly the crude transesterification product remaining in the reactor after the ester intercharge or the pentaerythrite phosphite purified by distillation under reduced pressure.

Some of the novel phosphites are viscous liquids at room temperature; often and preferably, however, they are white solid products, some of which have wax-like characteristics. Most interesting are the latter having flow-drop-points of from 35° to 100° C., since in addition to their stabilization effect, they influence favorably the properties of the products made of polymer molding compositions containing such wax-like phosphites.

In the phosphites of the formula

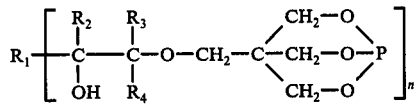

$n$ is 1 or 2.

In the case where $n$ is 1, $R_1$ through $R_4$ stand for identical or different radicals up to three of which may be hydrogen atoms. The remaining radicals R are either a phenyl or naphthyl group optionally substituted by 1 or 2 alkyl or isoalkyl groups having from 1 to 9, preferably 1 to 4, carbon atoms, or by up to 4 chlorine atoms, that is, for example, a phenyl, tolyl, xylyl, tert.-butylphenyl, nonylphenyl, chlorophenyl, naphthyl or chloronaphthyl group; or a saturated or unsaturated cycloalkyl radical having from 5 to 12, preferably 5 to 7, carbon atoms which may carry the above alkyl groups or chlorine as substituents, such as a cyclopentyl, cyclohexyl, cycloheptyl, cyclooctyl or cyclododecyl radical. The total number of these phenyl, naphthyl or cycloalkyl radicals is preferably three at most, and especially two at most. Preferably, $R_1$ through $R_4$ may stand for a linear or branched alkyl radical having from 1 to 60, preferably 8 to 40, especially 10 to 30, carbon atoms, optionally being substituted by a phenyl, an alkylphenyl group having from 7 to 10 carbon atoms or a cycloalkyl group having from 5 to 12 carbon atoms, such as an ethyl, butyl, hexyl, octyl, decyl, dodecyl, tetradecyl, hexadecyl, octadecyl, eicosyl, docosyl, tetracosyl, hexacosyl, octacosyl, triacontyl, dotriacontyl, tetratriacontyl, hexatriacontyl, octatriacontyl, tetracontyl or dotetracontyl radical. The radicals $R_1$ through $R_4$ may optionally contain ether, thioether, carboxylic acid ester or epoxide groups, halogen substituents, preferably chlorine, or C=C bonds in addition. Furthermore, the radicals $R_2$ and $R_3$ may be common members of a saturated or unsaturated alkylene chain having from 3 to 10, preferably 3 to 6, carbon atoms, and this chain may optionally carry up to 3 alkyl substituents having from 1 to 4 carbon atoms, or an aryl substituent having 6 to 10 carbon atoms. The novel phosphites are furthermore characterized in that the total number of all carbon atoms contained in the radicals $R_1$ to $R_4$ is at least 4, preferably at least 8, but does not exceed 60.

In the case where the symbol $n$ of the formula represents 2, the radicals $R_2$ through $R_4$ are as defined for $n = 1$; $R_1$, however, is a bivalent organic radical.

By bivalent organic radical, there is to be understood in this connection:

(a) an alkylene chain having from 1 to 10, preferably 2 to 8 carbon atoms, optionally substituted by methyl or ethyl groups and optionally interrupted by ether, tioether or carboxylic acid ester groups. Examples are the methylene, ethylene, propylene, butylene, hexylene or octylene groups.

(b) a group of the formula —CH$_2$—O—A—O—CH$_2$—, wherein A stands for a phenylene or naphthylene radical optionally substituted by 1 or 2 alkyl groups having from 1 to 4 carbon atoms, or by 1 to 2 halogen atoms, preferably chlorine; or for an alkylene chain having from 2 to 12, preferably 2 to 6, carbon atoms, optionally substituted by methyl or ethyl groups and optionally interrupted by ether, thioether or carboxylic acid ester groups; or for a 1,3- or 1,4-dimethylenecyclohexane radical. A may represent alternatively an α, ω-diacylalkylene radical having from 3 to 12, preferably 4 to 10, carbon atoms, optionally substituted by methyl or ethyl groups and optionally interrupted by ether, thioether, carboxylic acid ester groups or C=C bonds, for example a succinic, glutaric, adipic, suberic, azelaic, sebacic, diglycolic or thiodiglycolic acid radical. Furthermore, A may be a diacylphenylene or diacylnaphthylene radical optionally substituted by 1 to 2 alkyl groups having from 1 to 4 carbon atoms, or by 1 to 4 halogen atoms, preferably chlorine, for example an o-, iso- or therephtalic acid radical, a tetrachloro-orthophthalic acid radical, a naphthalene-dicarboxylic acid radical or a chloronaphthalene-dicarboxylic acid radical.

(c) a group of the formula

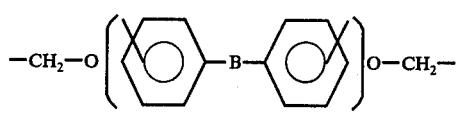

wherein B may represent an oxygen or sulfur atom, a —CO—, —SO— or

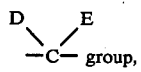

group, wherein D and E, being identical or different represent hydrogen atoms or alkyl groups having from 1 to 6 carbon atoms, for example methyl, ethyl, propyl or butyl groups, or they are common members of an alkylene chain having from 4 to 6 carbon atoms; and (d) a group of the formula

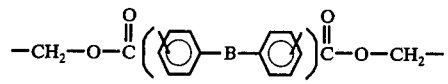

wherein B is as defined for c).

Also in the case of $n$ being 2, the total number of all carbon atoms contained in the radicals $R_1$ through $R_4$ is at least 4, preferably at least 8 and does not exceed 60.

Especially important are the radicals according to (c).

Some typical representatives of the phosphites of the invention are cited as follows, without, however, limiting the invention to these substances. Designations such as $C_{12/14}$-alkyl, $C_{18/22}$-alkyl, $C_{22/26}$-alkyl or $C_{\overline{30}}$-alkyl indicate that the products have been obtained by reaction of epoxide mixtures.

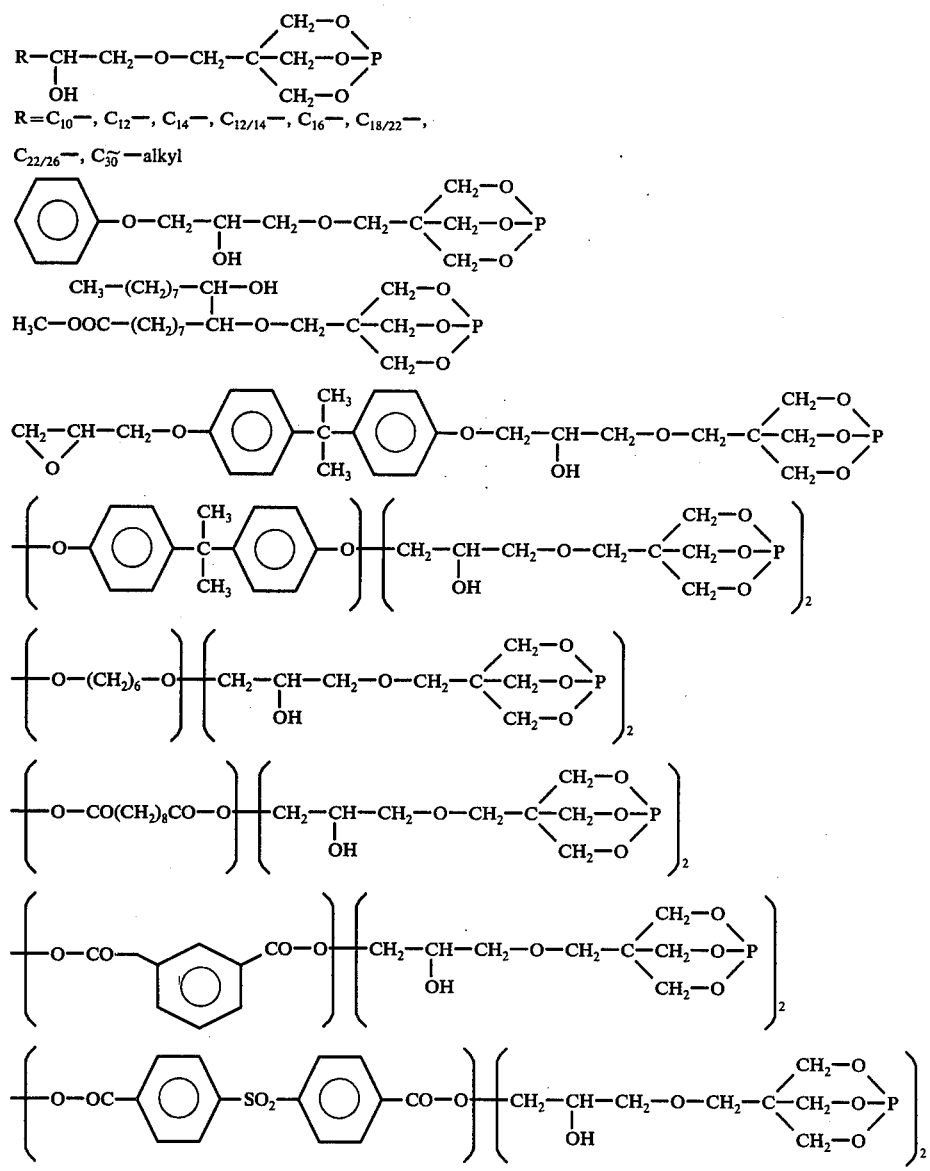

The above survey on a few typical representatives of the novel phosphites demonstrates the fact that an extraordinarily great number of most various expoxides may be used. Thus, for example, polyepoxides having more than 2 epoxy groups in the molecule may be reacted with pentaerythrite phosphite to form the corresponding polyphosphites.

The phosphites of the invention may be used in admixture with other generally known stabilizers, antioxidants, UV-stabilizing compounds, optionally also in the presence of, for example, lubricants, plasticizers, pigments, fillers or other additives. They are employed in amounts of from 0.01 to 10, preferably 0.05 to 2.0, and especially 0.1 to 1, parts by weight, relative to 100 parts by weight of polymer.

When chlorinated polymers, such, for example, as chloropolyethylene, hard and soft polyvinyl chloride, polyvinylidene chloride, polyvinylchloroacetate and vinyl chloride-α-olefincopolymers are processed, a substantially improved stability to heat and to light is achieved by adding the novel phosphites of the invention, in the presence of compounds known as stabilizers such, for example, as metal compounds, indoles substituted in the 2-position, preferaby 2-phenylindole, epoxide stabilizers and/or optionally polyhydric alcohols.

Suitable metal compounds known as stabilizers are, for example, Ca, Ba, Sr, Zn, Cd, Mg, Al and Pb soaps of aliphatic carboxylic acids or oxycarboxylic acids having from 8 to 32 carbon atoms, preferably from 8 to 20 carbon atoms, salts of these metals with aromatic carboxylic acids of preferably from 7 to 12 carbon atoms, e.g. benzoates, salicylates as well as (alkyl)phenolates of these metals, the alkyl radical having from 1 to 12, preferably 1 to 6, carbon atoms. This range of compounds also includes organo-tin compounds, e.g. dialkyl-tin-thioglycolates and carboxylates as well as—optionally—neutral and basic lead salts of inorganic acids such, for example, as sulfuric acid and phosphorous acid.

Known epoxide stabilizers are, for example, higher epoxidized fatty acid triglycerides such, for example, as epoxidized soybean oil, tall oil or linseed oil, epoxidized butyloleate and higher epoxyalkanes.

Polyhydric alcohols are, for example, pentaerythritol, trimethylol propane, sorbitol or mannitol, i.e. preferably alcohols having from 5 to 6 carbon atoms and from 3 to 6 OH groups.

A stabilizer composition for processing halogenated polymer molding compositions consists, for example, of from 0.01 to 10, preferably 0.1 to 2.0, parts by weight of a phosphite of the invention, 0.1 to 10 parts by weight of a metal compound known as stabilizer, 0.1 to 10 parts by weight of a known epoxide stabilizer and 0 to 1 part by weight of a polyhydric alcohol.

The novel phosphites display also an excellent efficiency for stabilizing polymers or copolymers of olefins free from halogen. The stability of, for example, polypropylene to heat and to light is considerably improved by the addition of the phosphites of the invention, especially in admixture to phenolic and/or sulfidic stabilizers.

Suitable phenolic and sulfidic stabilizers are, for example, the generally known stabilizers against heat and light which are used in the processing of plastics, for example 3,5-ditertiarybutyl-4-hydroxyphenyl-propionic acid ester, 2,6-ditertiarybutyl-p-cresol, alkylidene-bis-alkyl-phenols, esters of bis-(4'-hydroxy-3'-tertiary-butylphenyl)-butyric acid, thiodipropionic acid ester of fatty alcohols as well as dioctadecyl sulfide or dioctadecyl disulfide.

A synergistically efficient stabilizer composition for polymers or copolymers of olefins free from halogen consists, for example, of from 0.05 to 5, preferably 0.05 to 1.0, parts by weight of a phosphite according to the invention, from 0.05 to 3 parts by weight of a known phenolic stabilizer and/or from 0.1 to 3 parts by weight of a known sulfidic stabilizer. Special stabilizers against ultra-violet rays may also be added to the stabilizer composition in an amount of from 0.1 to 3 parts by weight, if necessary. Known ulta-violet absorbers are, for example, alkoxy-hydroxybenzophenones, hydroxyphenylbenzotriazoles, salicyclic acid phenol ester, benzoic acid hydroxyphenol ester, benzylidene malonic acid mononitrile ester as well as so-called "quenchers" such, for example, as nickel chelates, hexamethyl-phosphoric acid triamide or piperidine stabilizers.

Stabilizer compositions of the phosphites according to the invention and known stabilizers not only improve the stability of polyolefins, chloropolyolefins and chlorinated vinylpolymers, but impart also an improved stability to polyesters, polyamides, polyacrylonitrile, polycarbonates, polysiloxanes, polyethers, polyurethanes and others.

The following Examples illustrate the invention and demonstrate the advantages of the novel phosphites.

EXAMPLE 1

A four-necked flask having a capacity of 2 liters and provided with agitator, interior thermometer, gas inlet and reflux condenser is charged with 930 g of a mono-epoxy-alkane mixture having a chain length of $C_{26}$ to $C_{52}$ (about 97% of terminal epoxy groups, mean molecular weight 465, oxirane oxygen content 2.5%), and 328 g (2 mols) of pentaerythrite phosphite. The contents of the flask are heated to 90° to 100° C. under a weak nitrogen current. 2.6 g (0.01 mol) of tin-IV chloride are added dropwise to the melt obtained, and the reaction mixture is then stirred for 30 minutes at 90° to 100° C. Subsequently, the inner temperature is raised to 135°–140° C., and the reaction mixture is stirred at this temperature for 20 hours.

After cooling of the transparent melt having a slightly yellow color, 1250 g of pentaerythrite phosphite-β-hydroxy-$C_{26-52}$-alkyl ether in the form of a hard white wax having a flow/drop point of 81.5° to 83° C. (determined according to DGF M III 3 (57)) are obtained.

Residual oxirane oxygen content: 0.2% phosphorus content: 4.7%.

EXAMPLE 2

In the manner as described in Example 1, 620 g of a $C_{20-24}$-mono-epoxyalkane mixture (mean molecular weight 310, oxirane oxygen content 4.9%) and 328 g (2 mols) of pentaerythrite phosphite are reacted in the presence of 2.6 g (0.01 mol) of tin-IV chloride. 945 g of pentaerythrite phosphite-β-hydroxy-$C_{20-24}$-alkyl ether in the form of a white soft wax are obtained having a flow/drop point of 51.5°–52.5° C.

Residual oxirane oxygen content: 0.3%, phosphorus content: 6.1%.

EXAMPLE 3

According to the operation mode described in Example 1, 552 g (3 mols) of 1,2-epoxydodecane (oxirane oxygen content 8.6%) and 492 g (3 mols) of pentaerythrite phosphite are reacted in the presence of 3.03 g (0.03 mol) of triethylamine. After a 20 hour reaction time, the reflux condenser is replaced by a descending cooler, and the reaction mixture is stirred for a further hour at 135°–140° C. under reduced pressure of 0.1 mm produced by an oil pump, in order to eliminate volatile substances. After this period, 27.6 g of unreacted 1,2-epoxydodecane are collected in the cooling trap inserted between reactor flask and oil pump. 1014 g of pentaerythrite phosphite-β-hydroxydodecyl ether remain in the reactor vessel in the form of a colorless, transparent, very viscous liquid which, on prolonged standing, crystallizes to form a soft crystalline mass having a flow/drop point of 35°–40° C.

Residual oxirane oxygen content: 0.2%; phosphorus content: 8.4%.

EXAMPLE 4

According to the operation mode described in Example 1, 780 g of commercial epoxidized soybean oil (epoxy equivalent weight 260) and 492 g (3 mols) of pentaerythrite phosphite are reacted in the presence of 3.9 g (0.015 mol) of tin-IV chloride.

1270 g of the epoxide-pentaerythrite phosphite adduct are obtained in the form of a nearly colorless transparent soft resin.

Residual oxirane oxygen content: 2.1%; phosphorus content: 6.8%.

EXAMPLE 5

According to Example 1, 570 g of a commercial bisglycidyl ether of 2,2-(4,4'-dihydroxydiphenyl)-dimethylmethane known also as "Bisphenol A" (epoxy equivalent weight 190) and 492 g (3 mols) of pentaerythrite phosphite are reacted in the presence of 3.9 g (0.015 mol) of tin-IV chloride.

1060 g of the epoxide-pentaerythrite phosphite adduct are obtained in the form of a slightly yellow, transparent, brittle resin.

Residual oxirane oxygen content: 0.3%; phosphorus content: 9.2%.

EXAMPLE 6

In order to test the resistance to hydrolysis of the novel phosphites as compared to that of four commercial products, the following operations are carried out:

5 g of phosphite are heated to boiling point in 100 ml of distilled water; after having boiled for 20 to 60 minutes, the reaction batch is cooled and its content in phosphorous acid is determined in the aqueous solution by means of tritration with aqueous 0.1 N-sodium hydroxide solution. The degree of hydrolysis of the phosphite submitted to the test is determined as 100 $x/y$, $x$ being the actual volume of 0.1 N-NaOH consumed and $y$ beig the theoretical volume of this agent calculated for complete hydrolysis of the phosphite to yield phosphorous acid.

| Phosphite | Degree of hydrolysis in % after a boiling time of | |
|---|---|---|
| | 20 min | 30 min |
| a) Triphenylphosphite[1] | 84 | 100 |
| b) Tris(nonylphenyl)phosphite[1] | 57 | 92 |
| c) Diphenyl-isooctylphosphite[1] | 55 | 77 |
| d) Distearyl-pentaerythrityl-diphosphite[1] | 52 | 68 |

| Phosphite | Degree of hydrolysis in % after a boiling time of | |
|---|---|---|
| | 20 min | 30 min |
| Phosphite acc. to Example | | |
| e) 1 | 3 | 4 |
| f) 2 | 14 | 24 |
| g) 3 | 7 | 12 |
| h) 4 | 11 | 38 |
| i) 5 | 2 | 12 |

[1]commercial products as comparative substances

EXAMPLES 7 to 24

These Examples illustrate the stabilizing effect of phosphites of the present invention on the processing of polyvinyl chloride. The dynamic thermostability (Examples 7 to 15) and the static thermostability (Examples 16 to 24) were determined. The specified parts are parts by weight.

For each of a number of phosphites of the present invention, 100 parts of a mass-polyvinyl chloride having a K-value of 60 were mixed thoroughly with 0.2 parts of 2-phenylindole, 3 parts of epoxidized soybean oil, 0.25 parts of a complex calcium/zinc stabilizer (consisting of 42 weight % of calcium stearate, 30 weight % of zinc stearate, 22 weight % of pentaerythrite and 6 weight % of 2,5-di-t-butyl-4-methyl-phenol), 0.2 part of a montanic acid ester (acid number 18, saponification number 154), 0.3 part of stearyl stearate, 0.5 part of glycerol monostearate, and 0.5 part of the phosphite.

In order to determine the dynamic thermostability each mixture was applied on to a laboratory-scale twin-roller device heated to 180° C., and rolled out to a sheet within 1 minute at 20 rpm. At intervals of 10 minutes, spot samples were picked of these sheets, and their color shades compared with an internal color chart. The various tests were run until the rolled-out rough sheet had taken up a dark-brown to black shade.

In order to determine the static thermostability a rough sheet was first prepared from each mixture according to the description given above, and this sheet was rolled out on the twin-roller device at 180° C. for another 10 minutes' period. The sheet was then peeled off the roller and little plates of about 0.5 mm thickness and a diameter of 30 mm blanked therefrom. The sheets were wrapped in an aluminum sheet and tempered at 180° C. in a heating cabinet with air circulation. One specimen was selected every 10 minutes and its color shade compared with the color chart. The figures employed in the color chart have the following meaning:

1 = clear as water
2 = slightly yellowish
3 = distinctly yellow tint
4 = dark yellow-brown shade
5 = dark brown to black As demonstrated by the following Tables, as far as dynamic and static thermostability are concerned, the polyvinyl chloride stabilized by organic phosphites of the present invention is clearly superior in comparision to polyvinyl chloride stabilized with known phosphites and with mixtures free from phosphites.

| Example No. | Phosphite acc. to Example | Dynamic thermostability Discoloration of the rough sheet at a laminating time of | | | | | | | | | |
|---|---|---|---|---|---|---|---|---|---|---|---|
| | | 10' | 20' | 30' | 40' | 50' | 60' | 70' | 80' | 90' | 100' |
| | | | | | | to color no. | | | | | |
| 7 | 1 | 1 | 1–2 | 2 | 2–3 | 3 | 3 | 3–4 | 4 | 4–5 | 5 |
| 8 | 2 | 1 | 1–2 | 2–3 | 3 | 3–4 | 4 | 4–5 | 5 | | |
| 9 | 3 | 1 | 2 | 2–3 | 3 | 3 | 3–4 | 4 | 4–5 | 5 | |
| 10 | 4 | 1 | 2 | 2–3 | 3 | 3–4 | 4 | 4–5 | 5 | | |
| 11 | 5 | 1 | 1–2 | 2 | 3 | 3–4 | 4 | 4–5 | 5 | | |
| 12 (comp.) | 6a) | 1 | 2 | 2–3 | 5 | | | | | | |
| 13 (comp.) | 6c) | 1 | 2 | 3 | 5 | | | | | | |
| 14 (comp.) | 6d) | 1–2 | 2 | 2–3 | 3 | 3–4 | 4–5 | 5 | | | |
| 15 (comp.) | none | 2 | 2–3 | 3–4 | 5 | | | | | | |

| Example No. | Phosphite acc. to Example | Static thermostability Discoloration of rough sheet in drying cabinet at a tempering time of | | | | | | | | | | |
|---|---|---|---|---|---|---|---|---|---|---|---|---|
| | | 0' | 10' | 20' | 30' | 40' | 50' | 60' | 70' | 80' | 90' | 100' |
| | | | | | | | to color no. | | | | | |
| 16 | 1 | 1 | 1 | 1–2 | 2 | 2–3 | 3 | 3 | 3–4 | 3–4 | 4 | 4–5 |
| 17 | 2 | 1 | 1 | 2 | 2 | 2–3 | 3 | 3 | 3–4 | 3–4 | 5 | |
| 18 | 3 | 1 | 1–2 | 2 | 2–3 | 3 | 3 | 3 | 3–4 | 3–4 | 4 | 5 |
| 19 | 4 | 1 | 1–2 | 2 | 2 | 2 | 3 | 3 | 3–4 | 3–4 | 5 | |
| 20 | 5 | 1 | 1–2 | 2 | 2–3 | 2–3 | 3 | 3–4 | 3–4 | 4 | 5 | |
| 21 (comp.) | 6a) | 1 | 1–2 | 1–2 | 2 | 2–3 | 3 | 5 | | | | |
| 22 (comp.) | 6c) | 1 | 1–2 | 2 | 2 | 2 | 3 | 3–4 | 5 | | | |
| 23 (comp.) | 6d) | 1–2 | 2 | 2–3 | 2–3 | 3 | 3–4 | 3–4 | 4 | 5 | | |
| 24 (comp.) | none | 1 | 1–2 | 2 | 2–3 | 3 | 3–4 | 5 | | | | |

EXAMPLE 25

This example shows that the addition of a phosphite of the present invention to polypropylene improves considerably its stability to light and against alterations due to heat.

A powdery mixture consisting of
100 parts by weight of unstabilized polypropylene [$i_{5(230° C.)}$ about 8],
0.14 part by weight of octadecyl-3-(3',5'-di-tert.-butyl-4'-hydroxyphenyl)-propionate, and
0.10 part by weight of the pentaerythrite phosphite-β-hydroxy-$C_{25/52}$-alkyl ether prepared according to Example 1 was injection-molded on an injection molding machine to yield test plates measuring 60 × 60 × 1 mm. Test specimens were blanked from these plates.

The stability to light was determined by means of the Xeno-test device, type 150, produced by Messrs. Hanau Quarzlampen GmbH with the filter combination 6 IR + 1 UV as per DIN 53 387. (DIN = German Industrial Standard). The time of exposure to light, i.e. the period of time after which the absolute elongation at break had decreased to 10% was measured in hours. In the case of polypropylene stabilized with the product of Example 1 this time of exposure amounted to 818 hours. Comparative specimens which had been prepared according to the above-specified recipe—but without addition of one of the phosphite stabilizers of the invention—reached only 540 hours for this time of exposure.

The resistance to alteration under heat of injection molded test samples was measured approximately to the procedure described by DIN 53 383 at an air temperature of 140° C. In the case of polypropylene stabilized with the phosphite of Example 1, the resistance amounted to 54 days to total embrittlement; the resistance to alteration under heat of comparative samples without this stabilizer was 22 days.

EXAMPLE 26

In order to test the acute toxicity of the product according to Example 1, feeding tests on male albino mice according to the indications of Leopold Teer, Grundlagen der experimentellen Arzneimittelforschung, 1965 edition, were carried out. The $LD_{50}$ values were determined after administration in a 1% methylcellulose solution (Tylose ®). A $LD_{50}$ value of > 4000 mg/kg of body weight was the result.

We claim:
1. Phosphites of the formula

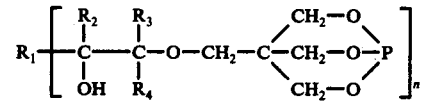

wherein n is 1 or 2, and where n is 1, $R_1$–$R_4$ are identical or different and are
 (a) 0–3 hydrogens
 (b) phenyl or naphthyl, or cycloalkyl of 5–12 carbons or said radicals substituted by alkyl of 1–9 carbons or by 1–4 chlorines,
 (c) linear or branched alkyl of 1–60 carbons or
 (d) $R_2$ and $R_3$ are identical and are links of a saturated or unsaturated alkyl- or aryl substituted alkylene chain, the alkylene chain having 3–10 carbons,
and the sum of all carbons of $R_1$–$R_4$ being 4–60; and where n is 2, $R_2$, $R_3$ and $R_4$ are as defined above and $R_1$ is a bivalent organic radical which is
 (a') an alkylene chain of 1–10 carbons unsubstituted or substituted by methyl or ethyl,
 (b') a group of the formula

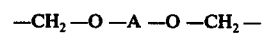

wherein A is (α) phenylene or naphthylene unsubstituted or substituted by 1-2 alkyls of 1-4 carbons or by 1-2 halogens,
(β) a alkylene chain of 2-12 carbons unsubstituted or substituted by methyl or ethyl.
(γ) 1,3 or 1,4-dimethylene cyclohexane,
(δ) αω-diacylalkylene of 3-12 carbons unsubstituted or substituted by methyl or ethyl, or
(ε) diacylphenylene or diacylnaphthylene,
(c′) a group of the formula

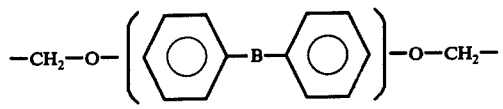

wherein B is —O—, —S—, —CO—, —SO$_2$ or

wherein D and E are identical or different and are hydrogen, alkyl of 1-6 carbons, or common members of an alkylene chain of 4-6 carbons, or
(d′) a group of the formula

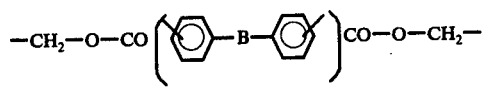

wherein B is as defined in (c′) above; and the sum of all carbons in $R_1$–$R_4$ is 4–60.

2. The phosphites as claimed in claim 1, wherein n is 1 and $R_1$ is a linear or branched alkyl of 6–58 carbons, $R_3$ and $R_4$ are hydrogen, $R_2$ is hydrogen, methyl or ethyl, and the sum of all carbons in $R_1$–$R_4$ is 6–60.

3. A plastic molding composition consisting essentially of an organic polymer selected from the group consisting of chloropolyethylene, polyvinylchloride, polyvinylidene chloride, polyvinylchloroacetate, vinylchloride-α-olefin copolymers, and polymers or copolymers of olefins free from halogen, and as stabilizer a phosphite of claim 1 in an amount of 0.1–10 parts by weight relative to 100 parts by weight of polymer.

4. Stabilizer combination for chlorinated polyolefins and chlorine containing vinyl homo- and copolymers, consisting of 0.01 to 10 parts by weight of a phosphite as claimed in claim 1, 0.1 to 10 parts by weight of a metal compound stabilizer, 0.1 to 10 parts by weight of an epoxide stabilizer, and 0 to 1 part by weight of a polyol, said epoxide stabilizer being an epoxidized fatty acid triglyceride or epoxidized butyloleate and said polyol being a polyhydric alcohol having from 5 to 6 carbons and from 3 to 6 hydroxyls.

5. Stabilizer combination with synergistic effect for polymers or copolymers of halogen-free olefins, consisting of 0.05 to 5 parts by weight of a phosphite as claimed in claim 1, 0.05 to 3 parts by weight of a phenolic stabilizer and/or 0.1 to 3 parts by weight of a sulfidic stabilizer selected from the group consisting of alkyl diesters of thiodipropionic acid, dialkyl sulfides and dialkyl disulfides, and 0 to 3 parts by weight of an ultraviolet stabilizer.